United States Patent [19]

Burger et al.

[11] 4,125,464
[45] Nov. 14, 1978

[54] METHOD AND APPARATUS FOR MULTIPLE DEVELOPMENT OF THIN-LAYER CHROMATOGRAPHY PLATES

[75] Inventors: Klaus Burger, Dormagen; Hans Mausberg, Neuss; Hubert Tengler, Dormagen, all of Germany

[73] Assignee: Bayer Aktiengesellschaft, Leverkusen, Germany

[21] Appl. No.: 841,237

[22] Filed: Oct. 11, 1977

[30] Foreign Application Priority Data

Oct. 15, 1976 [DE] Fed. Rep. of Germany ....... 2646640

[51] Int. Cl.² ............................................. B01D 15/08
[52] U.S. Cl. ................................. 210/31 C; 210/198 C
[58] Field of Search ........................... 210/31 C, 198 C

[56] References Cited

U.S. PATENT DOCUMENTS

3,857,784  12/1974  Martinez ........................... 210/198 C
3,864,250  2/1975  Perry ................................ 210/198 C

*Primary Examiner*—John Adee
*Attorney, Agent, or Firm*—Sprung, Felfe, Horn, Lynch & Kramer

[57] ABSTRACT

Method and apparatus for the automatic multiple development of thin-layer chromatography plates. Instead of drying the plates by irradiation a laminar stream of inert gas is passed over the plate. Substances, which decompose at higher temperature, may be treated by chromatography, whereby reproducibility and sensitivity are higher and the productivity is increased.

4 Claims, 1 Drawing Figure

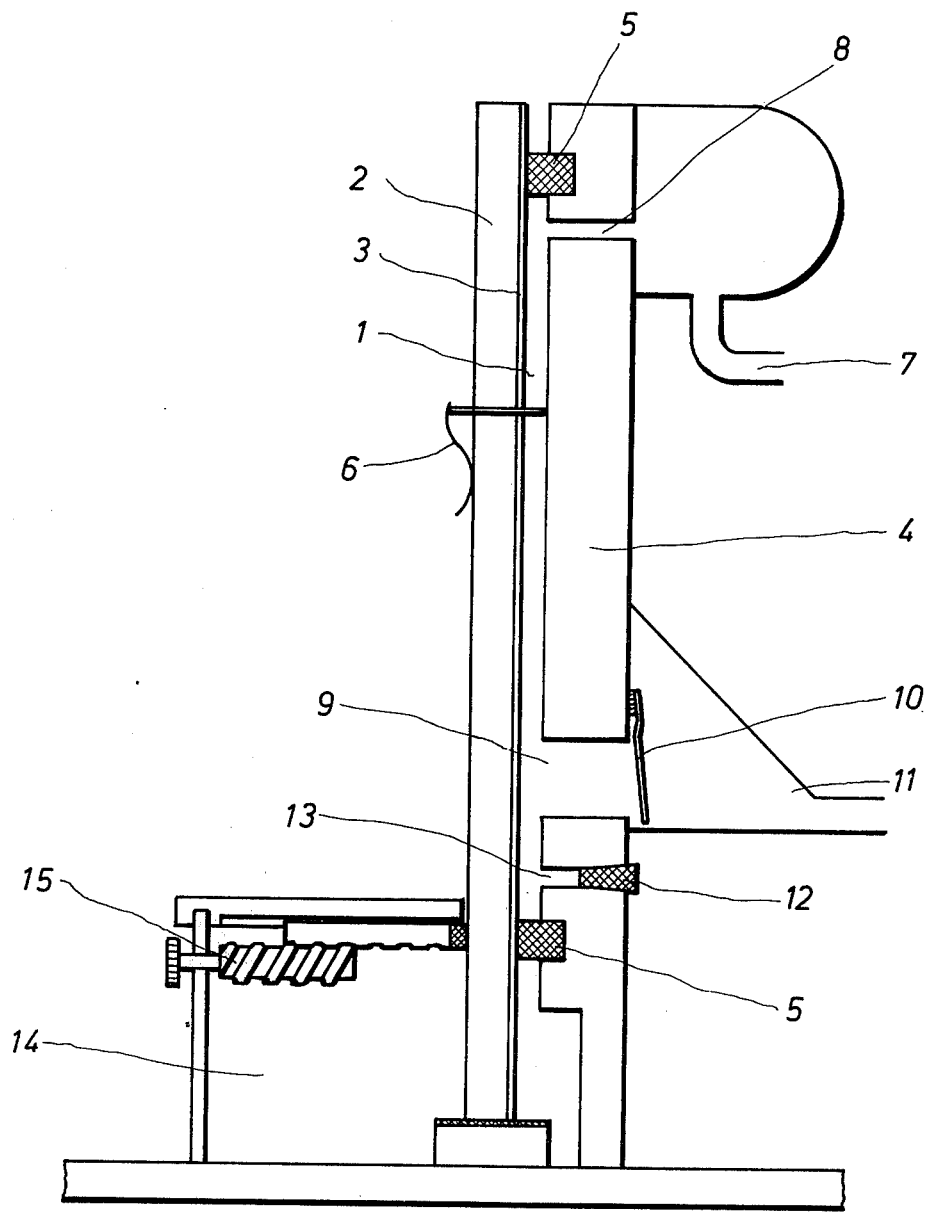

METHOD AND APPARATUS FOR MULTIPLE DEVELOPMENT OF THIN-LAYER CHROMATOGRAPHY PLATES

This invention relates to a method and an apparatus for automatically carrying out multiple development of thin-layer chromatography plates in which, after applying the substance to be analysed, the plate is brought into contact with the mobile phase and development is thus initiated, distribution is interrupted by drying the thin-layer chromatography plate after a pre-selected migration of the solvent front, and the cycle of development and drying is repeated several times.

Automated multiple development is known in thin-layer chromatography. Methods and instruments are described in the Journal of Chromatographic Science 11 (1973), 447/453, as are the advantages over conventional thin-layer chromatography (velocity and sensitivity). The thin-layer chromatography plates are dried by irradiation using quartz lamps.

Although this irradiation allows for automatic multiple development, substantial disadvantages have to be taken into consideration. Drying temperatures must not fall below 60° C., even in the case of low evaporation rates of low-boiling eluants, particularly if the plate remains in contact with the eluant for the drying period, and the constantly flowing mobile phase therefore also has to be evaporated. In the case of mobile phases with higher boiling points, the drying temperature must be considerably higher, causing the decomposition of the substances which are finely dispersed in the sorption agent. For this reason the majority of plant protective agents, for example, cannot be treated by chromatography by this method and using this known apparatus.

In addition, this method has the disadvantages of the sorption agent not being heated sufficiently uniformly and thus being activated unevenly during the drying treatment, and of involving different degrees of evaporation of individual eluant components during development. This results in an irregular solvent front and inclined zones of material. Moreover, time is wasted after each stage of drying until the sorption agent is sufficiently cool again.

An object of the invention is to avoid the disadvantages encountered when drying the sorption agent.

This object is achieved by a method which involves passing a laminar stream of inert gas over the plate for the drying treatment. The object is achieved in an apparatus by providing a gas inlet slit above the thin layer chromatography plate and by sealing the space in front of the thin layer chromatography plate which is thus separated in gas-tight manner from the eluant container. The advantages thus obtained are a wider field of application, higher productivity and greater sensitivity and reproducibility.

In a preferred embodiment of the method according to the invention, the inert gas stream is heated.

In the apparatus according to the invention for carrying out the method, the thin layer chromatography plate remains quite cold or is only slightly heated by the heated inert gas stream. The thermal stress is never so great that it causes decomposition of the substance to be analysed. A heated inert gas stream can readily replace the heat of evaporation on the sorption agent. With substances which are not sensitive to heat, the temperature of the inert gas stream may be regulated so that the drying period is reduced, without giving rise to long rest periods, until the eluant begins to migrate again, thus saving up to 75% in time. It is thus possible to use substances which cannot be thermally stressed in this method of automatic analysis. It is even possible to examine substances which change in air, because of the closed developing chamber and by making a suitable choice of inert gas, as well as the possibility of applying the samples to the layer through openings in the developing chamber while the inert gas stream is fed through the chamber.

The surfaces to be dried are precisely delimited by the limits of the chamber and the air control and the samples to be analysed can thus be focused on the starting line of the chromatogram. The solvent front is straight; the zones of substances are horizontal; the reproducibility is high.

An embodiment of the apparatus according to the invention is illustrated in the accompanying drawing by way of example and is described in more detail below:

A thin layer chromatography plate 2 bearing the sorption agent 3 is located in a housing 1, one side of which is formed by the thin-layer chromatography plate 2 itself and the opposite side of which is formed by a covering plate 4. Detachable seals 5 composed of inert material, preferably Teflon or refined steel, form the "frame of the housing" and project by at least 0.05 to 10 mm from the covering plate 4. The thin-layer chromatography plate 2 is pressed against the frame 5 by rotatable spring tongues 6. The housing 1 is thus sealed sufficiently from the surrounding air. The thin-layer chromatography plate 2 is preferably fixed vertically. The gas for rinsing the housing 1 and for drying the sorption layer 3 is supplied at 7 to a storage container which communicates with the housing 1 via a 0.1 to 10 mm wide gas inlet slit 8. A 0.5 mm wide slit 8 with a sealing frame which projects 0.2 mm from the covering plate has been found particularly suitable for producing a laminar gas stream over the sorption layer 3. A gas outlet slit 9 has an internal diameter of 5 mm; the issuing gas is fed through a valve 10 and led off at 11. Eluant vapours cannot escape. Openings 13 which may be sealed with a stopper 12 are arranged beneath the gas outlet slit 9, and the sample to be analysed is applied to the sorption agent 3 on the thin-layer chromatography plate 2 through these openings. As eluant container 14 is composed of glass or Teflon. The thin-layer chromatography plate 2 projects into the eluant container 14. The thin-layer chromatography plate 2 is pressed against the frame by a clamping mechanism 15 so as to prevent gas in the housing 1 from entering the covered eluant container 14. Preparatory measures and safety precautions required during chromatography are to be adopted but they are not described herein as they are known, as are the control instruments required for automatic operation.

What we claim is:

1. A method for the automatic multiple development of thin-layer chromatography plates comprising: forming a sealed chamber in conjunction with a portion of the active surface of a thin layer chromatography plate; contacting a portion of the plate not within the chamber with a mobile phase to initiate development; applying the substance to be analyzed to the chromatography plate by directing it into the sealed chamber before or just after the contacting step; interrupting the distribution by drying by introducing a laminar inert gas stream into the chamber after a preselected migration; repeating the steps of development and drying at least once while maintaining the sealed chamber.

2. A method according to claim 1, wherein the inert gas stream is heated.

3. An apparatus for the automatic multiple developments of thin layer chromatography plates comprising: means receptive of a thin layer chromatography plate for defining a sealed chamber with a portion of the active surface of the plate, said means including a covering plate, sealing means disposed between the covering plate and the chromatography plate to define the periphery of the chamber and means for biasing the two plates together to maintain the sealing action of the sealing means; a container for a mobile phase positioned with respect to the covering plate to receive a portion of the chromatography plate which is not within the chamber whereby the container and chamber are sealed off from each other; a sealable opening into the chamber for applying the substance to be analyzed to the chromatography plate; gas discharge means in communication with the chamber; and a gas inlet slit disposed above the gas discharge means.

4. An apparatus according to claim 3, wherein the gas discharge means comprises a gas outlet slit and a valve.

* * * * *